United States Patent [19]

Sanders et al.

[11] 4,031,161

[45] June 21, 1977

[54] PROCESS FOR PRODUCING MIXTURE CONTAINING 4-(4'-METHYL-4'-HYDROXYAMYL)-Δ³-CYCLOHEXENE CARBOXALDEHYDE

[75] Inventors: James Milton Sanders, Eatontown; William I. Taylor, Summit; Ira D. Hill, Locust; John J. Kryschuk, Howell, all of N.J.

[73] Assignee: International Flavors & Fragrances Inc., New York, N.Y.

[22] Filed: June 9, 1976

[21] Appl. No.: 694,391

[52] U.S. Cl. .............................. 260/598; 252/522
[51] Int. Cl.² ....................................... C07C 45/00
[58] Field of Search ................................ 260/598

[56] References Cited

UNITED STATES PATENTS 3,935,205  1/1976  Ochsner ..................... 260/598 X

*Primary Examiner*—Bernard Helfin
*Attorney, Agent, or Firm*—Arthur L. Liberman; Franklin D. Wolffe

[57] ABSTRACT

A process is described for reacting "myrac aldehyde" having the structure:

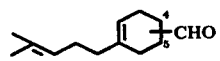

(which structure is representative of a mixture of two compounds, one where the carboxaldehyde is in the "4" position and the other wherein the carboxaldehyde is in the "5" position) with an acid hydrating agent at a temperature of from 0° up to 120° C, to produce a mixture containing a major proportion of 4-(4'-methyl-4'-hydroxyamyl)-Δ³-cyclohexene carboxaldehyde and a minor proportion of 3-(4'-methyl-4'-hydroxyamyl)-Δ³-cyclohexene carboxaldehyde (otherwise termed "Lyral") having the structure:

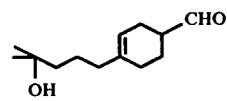

and a minor proportion of 3-(4'-methyl-4'-hydroxyamyl)-Δ³-cyclohexene carboxaldehyde having the structure:

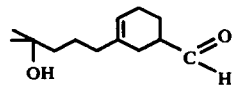

which mixture possesses a sweet, lilac-lily aromatic odor and isolating a mixture of the two carboxaldehydes. The products produced by the aforementioned process are useful in various aspects of perfumery.

10 Claims, 10 Drawing Figures

EXAMPLE XVI
Part (f)

GLC PROFILE

EXAMPLE XVI
Part (h)

GLC PROFILE

EXAMPLE XX

GLC PROFILE

EXAMPLE XX
NMR SPECTRUM OF LYRAL
SWEEP WIDTH 1500 Hz

EXAMPLE XX
NMR SPECTRUM OF MYRAC ALDEHYDE
SWEEP WIDTH 1500 Hz

EXAMPLE XX
IR SPECTRUM OF LYRAL

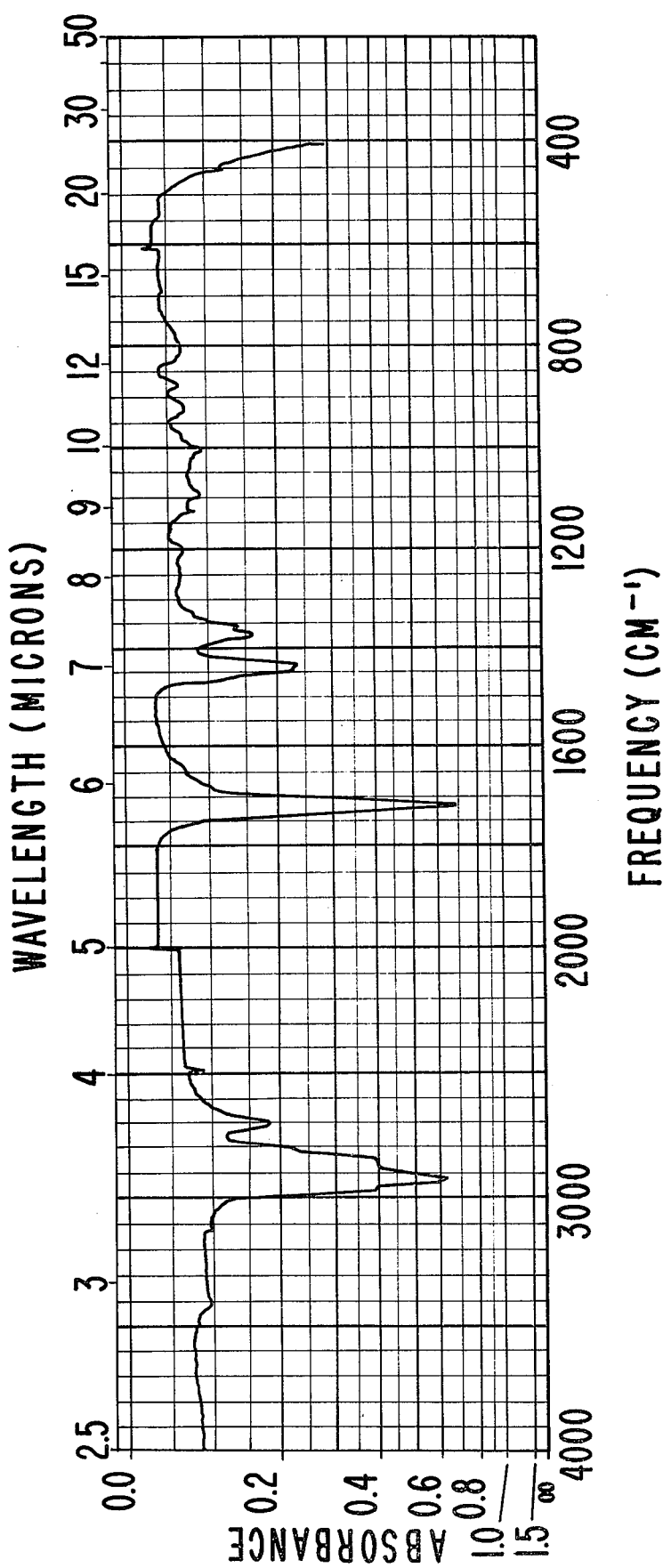

PROCESS FOR PRODUCING MIXTURE CONTAINING 4-(4'-METHYL-4'-HYDROXYAMYL)-Δ³-CYCLOHEXENE CARBOXALDEHYDE

BACKGROUND OF THE INVENTION

The present invention relates to a process for producing a mixture of 3- and 4-(4'-methyl-4'-hydroxyamyl)-Δ³-cyclohexene carboxaldehyde in good yields and under relatively mild conditions; and the uses in perfumery of the products produced by such process.

The mixture of 3- and 4-(4'-methyl-4'-hydroxyamyl)-Δ³-cyclohexene carboxaldehyde is a well known perfumery material having been produced by various processes including Diels-Alder reactions of acrolein having the structure:

with myrcenol having the structure:

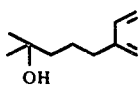

at high temperatures in the absence of catalyst or at low temperatures in the presence of a Lewis acid catalyst as described in an application for U.S. Pat. No. 620,354, filed on October 7, 1975. The mixture of 3- and 4-(4'-methyl-4'-hydroxyamyl)-Δ³-cyclohexene carboxaldehyde is indicated to be produced in U.S. Pat. No. 2,947,780 issued on Aug. 2, 1960, by means of reacting myrcenol in a sealed reactor and heating acrolein with myrcenol in a sealed reactor and heating the reaction mass to 150° C for a period of time (e.g. 4½ hours) accompanied by agitation. The reaction mass is then allowed to cool and the contents removed and subjected to fractional distillation.

U.S. Pat. No. 3,433,839 discloses a more complex process for preparing compounds having a structure similar to those prepared in the instant case. U.S. Pat. No. 3,433,839 discloses a process for producing a mixture of alicyclic hydroxyaldehydes which comprises:
i. photo-oxidizing myrcene to produce a mixture of its hydroperoxides;
ii. reducing the resulting mixture to produce a mixture of 2-methyl-6-methylene-3,7-octadiene-2-ol and 2-methyl-6-methylene-1,7-octadiene-3-ol; and
iii. reacting the thus-obtained mixture with a dienophile selected from the group consisting of acrolein and crotonaldehyde at 100° to 150° C for 3 to 6 hours to produce at least one mixture of alicyclic hydroxyaldehydes selected from the group consisting of, where said dienophile is acrolein, 4-(4'methyl-4'-hydroxy-2'-pentenyl)-3-cyclohexene-1-carboxaldehyde and 4-(4'-methyl-3'-hydroxy-4'-pentenyl)-3-cyclohexene-1-carboxaldehyde, and where said dienophile is crotonaldehyde, 4-(4'-methyl-4'-hydroxy-2'-pentenyl)-6-methyl-3-cyclohexene-1-carboxaldehyde and 4-(4'-methyl-3'-hydroxy-4'-pentenyl)-6-methyl-3-cyclohexene-1-carboxaldehyde.

British Pat. No. 1,419,243 discloses a process for the manufacture of aldehydes including the aldehydes produced in the instant case of the generic formula:

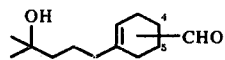

wherein the formyl group is present in either or both the 4- and 5- positions by hydrating an aminal of the formula:

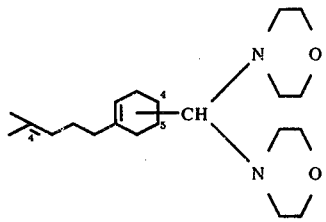

wherein the dimorpholine-methyl group is present in the 4- or 5-position, or a mixture of the 4- and 5-position isomers to the corresponding 4'-hydroxy compound and subsequently cleaving off the dimorpholino protecting group. It is indicated that the hydration of the aminal of the formula:

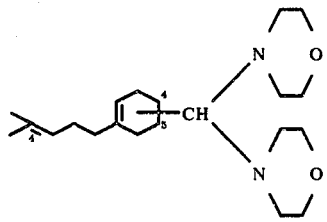

can be carried out according to "methods known . . . for example, by treatment with a non-oxidizing mineral acid such as sulphuric acid, phosphoric acid or hydrochloric acid . . . e.g. 50–70% sulphuric acid, 60–70% phosphoric acid or 28–33% hydrochloric acid." It is further indicated that the hydration can be carried out at a temperature of from approximately −20° C up to +30° C, preferably at approximately 0° C to approximately 20° C. The example on page 2 of British Patent 1,419,243 states that, when starting with 192 grams (1 mole) of myrac aldehyde which is a mixture of 3- and 4-(4'-methyl-3'-pentenyl)-Δ³-cyclohexene carboxaldehyde, 107 grams (51% yield) of a mixture of 3- and 4-(4'-methyl-4'-hydroxypentyl)-Δ³-cyclohexene carboxaldehyde (containing 35% of 3-(4'-methyl-4'-hydroxypentyl)-Δ³-cyclohexene carboxaldehyde) is produced.

Kagami, Canadian Journal of Chemistry, 52:125(1974) reports the hydration of the morpholine enamine of myrac aldehyde having the structure:

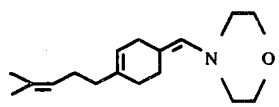

using 50% sulfuric acid. In Table 2 of this reference it is reported that myrac aldehyde per se is not hydrated to give compounds having the structure:

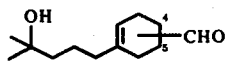

in the presence of 50% sulfuric acid at −2° to 10° C.

Thus, nothing in the prior art shows the possibilities of proceeding directly from compounds having the structure:

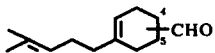

to compounds having the structure:

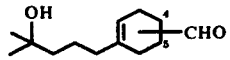

without going through the extra costly step of tying up the carboxaldehyde moiety with such groups as the morpholine group. Arctander, "Perfume and Flavor Chemicals, Aroma Chemicals" by Steffan Arctander, published in 1969, Volumn II at 2162 states that myrac aldehyde is a useful perfumery material but that "the hydroxylated aldehyde known under the name "lyral" . . . is far more successful than the title aldehyde but is in no way olfactorily related to it." Nevertheless, Arctander shows no way of "hydroxylating" myrac aldehyde without going through the costly step of "tying up" the carboxaldehyde moiety as is shown in British Pat. No. 1,419,243 and other related prior art.

BRIEF DESCRIPTION OF THE DRAWINGS

FIG. 10 is the Infrared spectrum for the myrac aldehyde produced according to the process of Example XIX.

THE INVENTION

Figure 1:
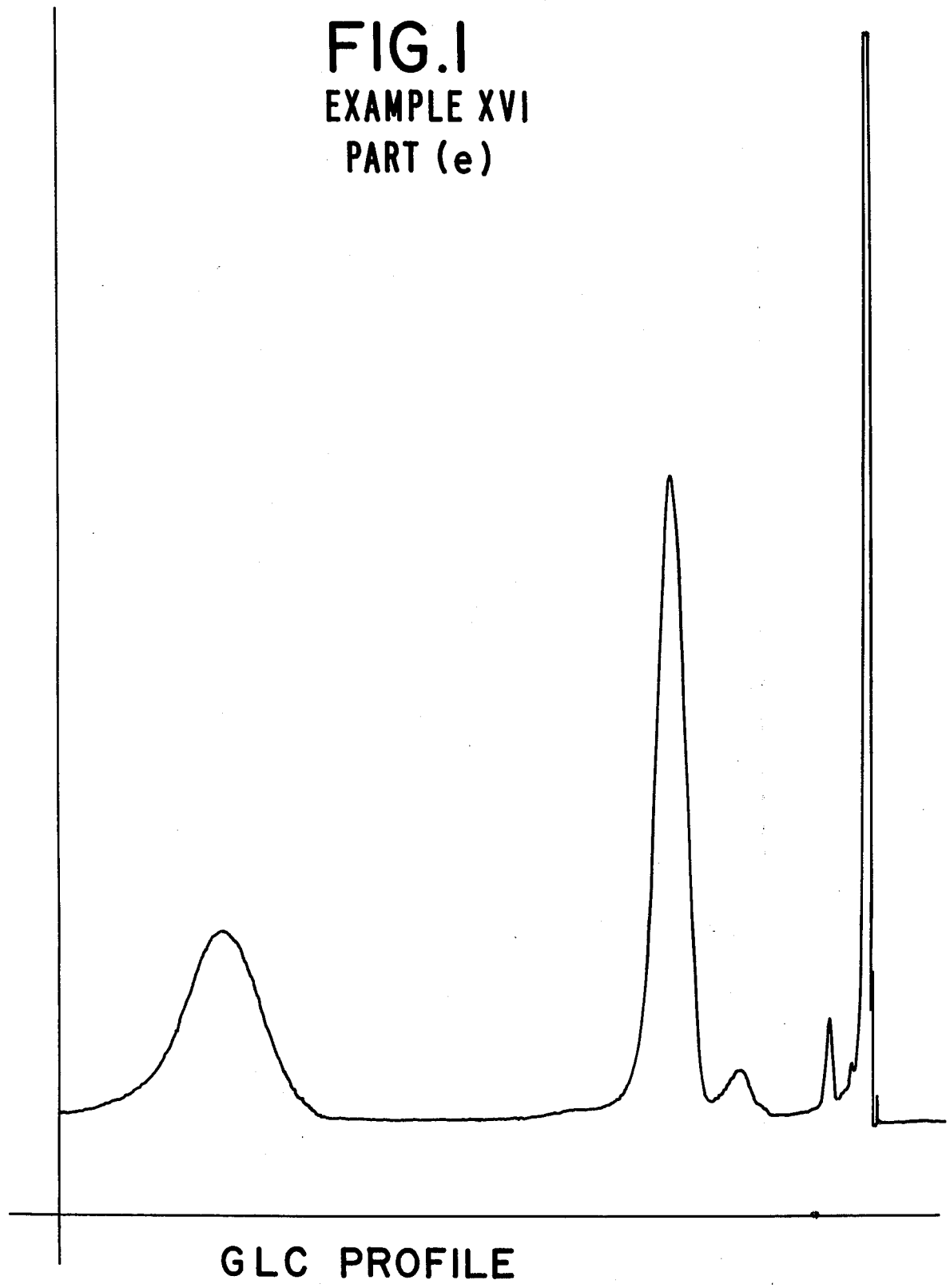
FIG. 1 is a GLC profile of the reaction product of Example XVI, Part E.

Surprisingly, it has been found that myrac aldehyde having the structure:

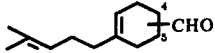

wherein the formyl group is present in the 4 position or a mixture of the 4 and 5 position isomers, can be directly hydrated to a mixture (at times, hereinafter referred to as lyral) containing a predominant quantity of 4-(4'-methyl-4'-hydroxyamyl)-$\Delta^3$-cyclohexene carboxaldehyde, by using an acidic hydration agent such as:

a. A mixture of at least one protonic acid and at least one water miscible, organic solvent;

b. One or a mixture of ion exchange resins;

c. One or a mixture of acidic polymerization catalysts; or d. One or a mixture of activated clays and, more preferably, one of the following acidic hydration materials:

i. mixture of lower alkanoic acid (e.g. formic acid and acetic acid) and p-toluene sulfonic acid;

ii. mixture of 30% aqueous sulfuric acid and tetrahydrofuran;

iii. mixture of 30% sulfuric acid and dimethyl formamide;

iv. mixture of 50% sulfuric acid and tetrahydrofuran;

v. mixture of 65% sulfuric acid and acetic acid;

vi. mixture of methane sulfonic acid and tetrahydrofuran;

vii. sulfonated co-polymer of styrene and divinyl benzene;

viii. mixture of (a) sulfonated co-polymer of styrene and divinyl benzene and (b) lower alkanoic acid;

ix. activated clay adsorbent;

x. silico-phosphoric acid polymerization catalyst; or xi. mixture of aqueous hydrochloric acid and a lower alkanol The temperature of reaction may vary from 0° C up to 120° C depending on the particular catalyst system used. An example of the sulfonated copolymer of styrene and divinyl benzene (containing about 4% divinyl benzene) is Dowex 50W-X4 produced by the Dow Chemical Company of Midland, Michigan. An example of an activated clay adsorbent is Filtrol 105 having the following properties:

| Particle Size Analysis | |
|---|---|
| By Roller (10 liters/min. air rate) | |
| 0–5 Microns, Wt. % | 8 |
| 0–20 Microns, Wt. % | 43 |
| By Tyler Standard Sieve | |
| Through 100 Mesh, Wt. % | 100 |
| Through 200 Mesh, Wt. % | 95 |
| Through 325 Mesh, Wt. % | 78 |
| Apparent Bulk Density, lb/cu.ft. | 42 |
| Free Moisture, Wt. % | 15 |
| Free and Combined Moisture, Wt. % (Loss at 1700° F) | 21 |
| Surface Area (BET Method), Sq.M/gm. | 300 |
| Acidity, Phenolphthalein, mg.KOH/gm. | 4.8 |
| Filter Rate, cc/min. | 38 |
| Oil Retention, Wt. % | 35 |

An example of the silico-phosphoric acid polymerization catalyst is UOP-SPA-2 polymerization catalyst manufactured by the Universal Oil Products Company of Des Plaines, Illinois.

The time of reaction is primarily a function of four variables:

1. temperature of reaction;
2. conversion desired;
3. particular hydration reagent utilized; and
4. concentration of hydration reagent in reaction mass.

In general, higher temperatures of reaction give rise to shorter required time of reaction, but too high a temperature of reaction and/or too long a time of reaction causes a diminution of conversion due to product decomposition. In general, higher concentration of hydration reagents in the reaction mass give rise to shorter time periods of reaction for a given conversion to the desired lyral reaction product. Thus, in general, the time of reaction may vary from 1 hour up to 48 hours.

The particular hydration reagent used in the process of our invention is surprisingly highly specific. Thus, a wise variety of hydration agents or hydration agent systems will be unworkable, for example:

64% sulfuric acid;
50% sulfuric acid;
30% sulfuric acid;
65% sulfuric acid-tetrahydrofuran mixture;
50% sulfuric acid-dimethyl formamide mixture; and
methane sulfonic acid.

The concentration of hydration material in the reaction mass varies from about 3% (when using such materials as polymerization catalyst) to about 50% when using hydration reagents such as a para-toluene sulfonic acid-formic acid mixture or a para-toluene sulfonic acid-acetic acid mixture. Preferably from about 3% up to about 10% by weight of the reaction mass of polymerization catalyst (e.g. silico-phosphoric acid) or cation exchange resin (e.g. Dowex 50W-X4) or activated clay adsorbent (e.g., Filtrol grade 105) is preferred, and from about 25% up to about 60% by weight of the reaction mass of hydration reagent such as 65% aqueous sulfuric acid-acetic acid mixture or 50% aqueous sulfuric acid-tetrahydrofuran mixture or 30% aqueous sulfuric acid-tetrahydrofuran mixture or 30% aqueous sulfuric acid-dimethyl formamide mixture or para-toluene sulfonic acid-formic acid mixture or methane sulfonic acid-tetrahydrofuran mixture is preferred. The ratio of protonic acid:co-solvent, e.g. sulfuric acid, methane sulfonic or para-toluene sulfonic acid: tetrahydrofuran, dimethyl formamide or acetic acid is preferably in the range of from about 1:5 up to about 5:1 on a dry basis and on a weight:weight ratio.

In summary, the advantages of the instant process for preparing reaction products containing major quantities of 4-(4'-methyl-4'-hydroxyamyl)-$\Delta^3$-cyclohexene carboxaldehyde are as follows:

1. The reaction can be carried out in standard vessels without pressure equipment and on a batch or a continuous basis;
2. The reaction can be carried out at moderate temperatures;
3. The reaction gives rise to high throughput, high conversion and high yields;
4. The noxious odor as well as the toxicity of certain Diels-Alder reagents such as acrolein does not exist as in the case of the prior art Diels-Alder reactions; and
5. The odor of morpholine or other amines (previously used to protect the carboxaldehyde during hydration) and problems concerning separation of such amines from the reaction mass at the end of the reaction do not exist.

The mixture containing 4-(4'-methyl-4'-hydroxyamyl)-$\Delta^3$-cyclohexene carboxaldehyde produced according to the process of our invention and one or more auxiliary perfume ingredients, including, for example, alcohols, other aldehydes, nitriles, esters, cyclic esters, and natural essential oils, may be admixed so that the combined odors of the individual components produce a pleasant and desired fragrance, particularly and preferable in lilac, floral, fougére, bouquet and rose fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however, the over-all sensory effect of the perfume composition will be at least the sum total of the effects of each of the ingredients. Thus, the mixture containing 4-(4'-methyl-4'-hydroxyamyl)-$\Delta^3$-cyclohexene carboxaldehyde produced according to the process of our invention can be used to alter, modify, or enhance the aroma characteristics of a perfume composition, for example, by utilizing or moderating the olfactory reaction contributed by another ingredient in the composition.

The amount of mixture containing 4-(4'-methyl-4'-hydroxyamyl)-$\Delta^3$-cyclohexene carboxaldehyde produced according to the process of our invention, which will be effective in perfume compositions as well as in perfumed articles and colognes depends on many factors, including the other ingredients, their amounts, and the effects which are desired. It has been found that perfume compositions containing as little as 0.01% of the mixture containing 4-(4'-methyl-4'-hydroxyamyl)-$\Delta^3$-cyclohexene carboxaldehyde produced according to the process of our invention, or even less (e.g., 0.005%) can be used to impart (or augment, enhance, or modify) a sweet, lilac-lily aromatic odor to (or in) soaps, cosmetics, or other products. The amount employed can range up to 70% of the fragrance components and will depend on considerations of cost, nature of the end product, the effect desired on the finished product, and the particular fragrance sought.

The mixture containing 4-(4'-methyl-4'-hydroxyamyl)-$\Delta^3$-cyclohexene carboxaldehyde produced according to the process of our invention is useful, taken alone or in compositions, or as an olfactory component in detergents and soaps, space odorants and deodorants, perfumes, colognes, toilet water, bath preparations such as bath oils and bath solids, hair preparations (such as lacquers, brilliantines, pomades and shampoos), cosmetic preparations (such as creams, deodorants, hand lotions and sun screens), and powders (such as talcs, dusting powders, face powders and the like). When used as an olfactory component, as little as 1% of the mixture containing 4-(4'-methyl-4'-hydroxyamyl)-$\Delta^3$-cyclohexene carboxaldehyde produced according to the process of our invention will suffice to impart a pleasant lilac-lily note to lilac, floral, fougére, bouquet, and rose formulations. Generally, no more than 8% of the mixture containing 4-(4'-methyl-4'-hydroxyamyl)-$\Delta^3$-cyclohexene carboxaldehyde produced according to the process of our invention, based on the ultimate end product, is required in the perfume composition.

In addition, the perfume composition or fragrance composition of our invention can contain a vehicle, or carrier for the mixture containing 3- and (predominantly) 4-(4'-methyl-4'-hydroxyamyl)-$\Delta^3$-cyclohexene carboxaldehyde produced according to the process of our invention. The vehicle can be a liquid such as a non-toxic alcohol, a nontoxic glycol, or the like. The carrier can also be an absorbent solid, such as a gum (e.g., gum arabic) or component for encapsulating the composition (such as gelatin).

The following Examples I-XXVIII are given to illustrate embodiments of the invention as it is presently preferred to practice it. It will be understood that these examples are illustrative, and the invention is not to be considered as restricted thereto except as indicated in the appended claims. The following Examples VII–XV and XX–XXVIII illustrate the utility in perfumery of the product produced by the process of the instant invention.

The following Examples A-K set forth attempted methods for preparation of mixtures containing high proportions of a mixture of 3- and 4-(4'-methyl-4'-hydroxyamyl)-$\Delta^3$-cyclohexene carboxaldehyde which methods were unsuccessful.

EXAMPLE A

ATTEMPTED PREPARATION OF MIXTURE OF 3- AND 4-(4'-METHYL-4'-HYDROXYAMYL)-$\Delta^3$-CYCLOHEXENE CARBOXALDEHYDE A solution is prepared by adding 50 grams of concentrated sulfuric acid to 50 grams of water. The resulting 50% sulfuric acid solution is cooled to 20° C and placed in a 250 ml reaction flask equipped with stirrer, thermometer, reflux condenser and addition funnel. With stirring, over a period of 1 hour, 60 grams of myrac aldehyde is added. Myrac aldehyde has the structure:

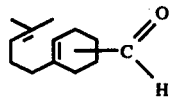

The reaction mass is stirred at a temperature of 20°–25° C for a period of 5 hours. GLC, NMR and Infrared analyses confirm that no conversion to 3- or 4-(4'-methyl-4'-hydroxyamyl)-$\Delta^3$-cyclohexene carboxaldehyde occurs. The same process is repeated except that a temperature of 50–55° C is used. No reaction takes place. The same reaction is repeated except that a temperature of 75° C is used and again, no reaction takes place.

EXAMPLE B

ATTEMPTED PREPARATION OF A MIXTURE OF 3-AND 4-(4'-METHYL-4'-HYDROXYAMYL)-$\Delta^3$-CYCLOHEXENE CARBOXALDEHYDE Into a 500 ml reaction flask equipped with stirrer and thermometer the following materials are placed:

| Ingredient | Quantity |
|---|---|
| myrac aldehyde | 50 grams |
| water | 50 grams |
| tetrahydrofuran | 500 grams |

With stirring, 20 grams of concentrated sulfuric acid is added and stirring is continued while the reaction mass temperature is maintained at 25° C. No reaction takes place.

The same reaction is carried out except that the reaction temperature is 50° C. No reaction takes place.

The same reaction is carried out except that the reaction temperature is 70° C and 30 grams of concentrated sulfuric acid is used. In this case conversion to a mixture of 3- and 4-(4'-methyl-4'-hydroxyamyl)-$\Delta^3$-cyclohexene carboxaldehyde is between 2 and 5%.

EXAMPLES C-K

In the following examples the given mixtures are intimately admixed at the conditions indicated; but in all cases no 3- or 4-(4'-hydroxyamyl)-$\Delta^3$-cyclohexene carboxaldehyde is formed:

| Example | Reaction Mixture | Reaction Conditions |
|---|---|---|
| C | 4 gms. myrac aldehyde<br>2.5 gms. water<br>30 gms. tetrahydrofuran<br>0.5 gms. concentrated sulfuric acid | reflux 5 hours |
| D | 4 gms. myrac aldehyde<br>4 gms. water<br>10 gms. tetrahydrofuran<br>2 gms. concentrated sulfuric acid | reflux 5 hours |
| E | 75 gms. of 64% sulfuric acid<br>25 gms. myrac aldehyde | −20° C for 2 hrs. |
| F | 5 gms. myrac aldehyde<br>1 gm. tetrahydrofuran<br>5 gms. of 64% sulfuric acid | reflux at 120° C for 30 minutes |
| G | 20 gms. myrac aldehyde<br>5 gms. dimethyl formamide<br>5 gms. water<br>5 gms. concentrated sulfuric acid | 55° C for 30 min. |
| H | 1.5 gms. myrac aldehyde<br>1.0 gms. dimethyl formamide<br>0.5 gms. concentrated sulfuric acid | 50° C for 30 min. |
| J | 1.5 gms. myrac aldehyde<br>1.0 gms. dimethyl formamide<br>0.5 gms. of 50% sulfuric acid | 50° C for 30 min. |
| K | 1.5 gms. myrac aldehyde<br>1.0 gms. dimethyl formamide<br>0.5 gms. of 50% sulfuric acid | 28° C for 30 min. |

EXAMPLE I

PREPARATION OF A MIXTURE OF 3- AND 4-(4'-METHYL-4'-HYDROXY-AMYL)-$\Delta^3$-CYCLOHEXENE CARBOXALDEHYDE Reaction:

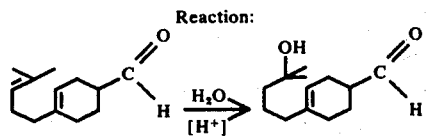

Into a 500 ml Erlenmeyer flask equipped with thermometer, magnetic stirrer and reflux condenser the following materials are mixed:

| Ingredient | Quantity |
|---|---|
| myrac aldehyde | 100 grams |
| water | 50 grams |
| Dowex®50W-X4 cation exchange resin (sulfonated co-polymer of styrene and divinyl benzene containing 4% divinyl benzene monomeric units produced by the Dow Chemical Company of Midland, Michigan; moisture content 65.3%; 50–100 | |

| Ingredient | Quantity |
|---|---|
| mesh) | 10 grams |

Samples are taken at 30-minute or 1-hour time intervals as indicated below and analyzed for the percentage of a mixture of 3- and 4-(4'-methyl-4'-hydroxyamyl)-$\Delta^3$-cyclohexene carboxaldehyde using GLC analysis (SE-30 column). The following table sets forth time, temperature and percent reaction product:

| Time | Temperature | % Mixture of 3- and 4-(4'-Methyl-4'-Hydroxyamyl)-$\Delta^3$-Cyclohexene Carboxaldehyde |
|---|---|---|
| 0 | 22° C | — |
| 1 hour | 23° C | 0 |
| 2 hours | 90° C | 0 |
| 3 hours | 95° C | 1.2% |
| 4 hours | 95° C | 1.8% |
| 5 hours | 100° C | 2.8% |
| 6 hours | 100° C | 2.8% |
| 7 hours | 100° C | 2.8% |
| 8 hours | 100° C | 2.8% |
| 9 hours | 100° C | 2.8% |
| 10 hours | 100° C | 2.8% |
| 11 hours | 100° C | 2.8% |
| 12 hours | 100° C | 2.8% |
| 22 hours | 21° C | 4.9% |
| * | | |
| 24 hours | 24° C | 4.8% |
| 26 hours | 25° C | 4.6% |
| 29½ hours | 64° C | 5.4% |
| 27½ hours | 103° C | 9.1% |
| 31½ hours | 100° C | 3.7% |
| 33½ hours | 100° C | 2.0% |
| 35½ hours | 100° C | 0.1% |
| 36½ hours | 100° C | complete decomposition |

*At this point 40 grams of 90% formic acid is added to the reaction mass.

EXAMPLE II

PREPARATION OF A MIXTURE OF 3- AND 4-(4'-METHYL-4'-HYDROXYAMYL)-$\Delta^3$-CYCLOHEXENE CARBOXALDEHYDE Reaction:

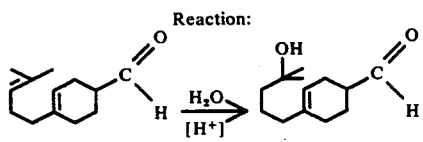

Into a 1 liter reaction flask equipped with stirrer, thermometer, addition funnel and reflux condenser is placed 185 grams of a 33% aqueous sulfuric acid solution. The sulfuric acid solution is heated to 40° C. Over a period of 1 ½ hours, while maintaining the temperature at 40° C, 220 grams of myrac aldehyde is added to the sulfuric acid solution from the addition funnel. The reaction mass is then maintained at 43° C for a period of 14 hours, at the end of which period of time it is determined by GLC analysis that 1.5% mixture of 3- and 4-(4'-methyl-4'-hydroxyamyl)-$\Delta^3$-cyclohexene carboxaldehyde is formed. At this point 10 ml tetrahydrofuran is added to the reaction mass. The reaction mass is then heated for a period of 14 hours at temperatures in the range of 43°-50° C whereupon it is determined that 2.8% mixture of 3- and 4-(4'-methyl-4'-hydroxyamyl)-$\Delta^3$-cyclohexene carboxaldehyde is formed. The reaction mass is then maintained at 24° C for 8 hours at the end of which period it is determined that 4.0% mixture of 3- and 4-(4'-methyl-4'-hydroxyamyl)-$\Delta^3$-cyclohexene carboxaldehyde is formed. At this point an additional 100 ml tetrahydrofuran is added. The reaction mass is then refluxed for a period of 12 hours at 74°-75° C at the end of which period of time it is determined that 13.9% mixture of 3- and 4-(4'-methyl-4'-hydroxyamyl)-$\Delta^3$-cyclohexene carboxaldehyde is formed.

The reaction mass is then washed with water followed by saturated aqueous sodium carbonate. The solvent is removed under reduced pressure and the resulting material is determined by GLC analysis to contain 14.8% mixture of 3- and 4-(4'-methyl-4'-hydroxyamyl)-$\Delta^3$-cyclohexene carboxaldehyde.

EXAMPLE III

PREPARATION OF A MIXTURE OF 3- AND 4-(4'-METHYL-4'-HYDROXYAMYL)-$\Delta^3$-CYCLOHEXENE CARBOXALDEHYDE Reaction:

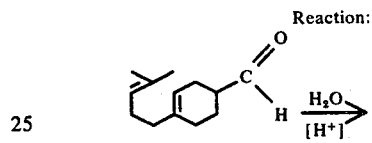

Into a 1 liter reaction flask equipped with stirrer, thermometer, addition funnel and reflux condenser the following materials are added:

| Ingredient | Quantity |
|---|---|
| para-toluene sulfonic acid | 38 grams |
| 90% aqueous formic acid | 180 grams |

The contents of the reaction vessel is stirred until complete solution is effected. The reaction mass is then cooled to 7° C and addition of myrac aldehyde is commenced. 300 grams of myrac aldehyde is then added to the reaction mass over a period of 2 ½ hours while maintaining the reaction mass at a temperature of between 5° and 10° C. At the end of the 2 ½ hour period, GLC analysis indicates formation of approximately 10% mixture of 3- and 4-(4'-methyl-4'-hydroxyamyl)-$\Delta^3$-cyclohexene carboxaldehyde. The temperature of the reaction mass is then raised to about 24° C and maintained thereat for a period of 4 hours at which time the percent of mixture of 3- and 4-(4'-methyl-4'-hydroxyamyl)-$\Delta^3$-cyclohexene carboxaldehyde in the reaction mass is determined to be 20%. The reaction mass is then cooled to 9° C, and 50 grams of water is added thereto. The reaction mass is stirred for a period of 1 hour while maintaining it at 9°-10° C at the end of which time 30.7% mixture of 3- and 4-(4'-methyl-4'-hydroxyamyl)-$\Delta^3$-cyclohexene carboxaldehyde is determined to be present. The reaction mass is then stirred at 20°-23° C for a period of 9 hours without any apparent change in the percent of mixture of 3-and 4-(4'-methyl-4'-hydroxyamyl)-$\Delta^3$-cyclohexene carboxaldehyde. The reaction mass is then washed with water and saturated aqueous sodium carbonate solution, and the solvent is stripped off. The stripped crude material is ascertained to contain 49.8% mixture of 3- and 4-(4'-methyl-4'-hydroxyamyl)-$\Delta^3$-cyclohexene carboxaldehyde.

EXAMPLE IV

PREPARATION OF A MIXTURE OF 3- AND 4-(4'-METHYL-4'-HYDROXYAMYL)-Δ³-CYCLOHEXENE CARBOXALDEHYDE

Reaction:

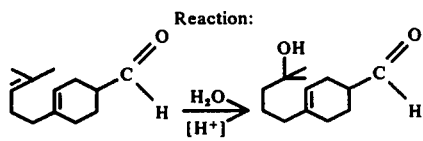

Into a 500 ml reaction flask equipped with a stirrer, thermometer, addition funnel and reflux condenser, the following materials are added:

| Ingredients | Quantity |
|---|---|
| water | 50 grams |
| myrac aldehyde | 250 grams |
| silico-phosphoric acid polymerization catalyst UOP-SPA-2 (manufactured by Universal Oil Prod. Corp. of Des Plaines, Ill.) | 10 grams |

The contents of the reaction flask are stirred at room temperature for a period of 2 hours at which time no formation of a mixture of 3- and 4-(4'-methyl-4'-hydroxyamyl)-Δ³-cyclohexene carboxaldehyde takes place. The reaction mass is then raised to 50° C and maintained thereat for a period of 2 hours at which time no formation of a mixture of 3- and 4-(4'-methyl-4'-hydroxyamyl)-Δ³-cyclohexene carboxaldehyde takes place. The contents of the reaction mass are then cooled and 50 grams of formic acid are added at room temperature. The reaction mass is then stirred at room temperature for a period of 8 hours at which time the reaction mass is heated to 70° C and maintained thereat for a period of 4 hours. The reaction mass is then heated to reflux for a period of 11 hours at which time it is determined by GLC analysis to contain 9% of a mixture of 3- and 4-(4'-methyl-4'-hydroxyamyl)-Δ³-cyclohexene carboxyaldehyde.

EXAMPLE V

PREPARATION OF A MIXTURE OF 3- AND 4-(4'-METHYL-4'-HYDROXYAMYL)-Δ³ CYCLOHEXENE CARBOXALDEHYDE

Reaction:

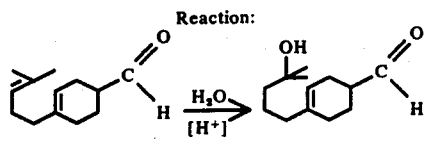

Into a 500 ml reaction flask equipped with a stirrer, thermometer, addition funnel and reflux condenser, the following materials are added:

| Ingredient | Quantity |
|---|---|
| Filtrol 105 (An activated clay adsorbent produced by the Filtrol Corporation having the following properties: Particle Size Analysis By Roller (10 liters/min. air rate) | 10 grams |
| 0-5 Microns, Wt. % | 8 |
| 0-20 Microns, Wt. % | 43 |
| By Tyler Standard Sieve | |
| Through 100 Mesh, Wt.% | 100 |
| Through 200 Mesh, Wt.% | 95 |
| Through 325 Mesh, Wt. % | 78 |
| Apparent Bulk Density, lb/cu.ft. | 42 |
| Free Moisture, Wt.% | 15 |
| Free and Combined Moisture, Wt.% (Loss at 1700° F) | 21 |
| Surface Area (BET Method), Sq.M/gm. | 300 |
| Acidity, Phenolphthalein, mg.KOH/gm. | 4.8 |
| Filter Rate, cc/min. | 38 |
| Oil Retention, Wt.% | 35 |
| water | 50 grams |
| myrac aldehyde | 250 grams |

The reaction mass is stirred at room temperature for a period of 2 1/2 hours at the end of which time no formation of 3- or 4-(4'-methyl-4'-hydroxyamyl)-Δ³-cyclohexene carboxaldehyde takes place. The reaction mass is then maintained for a period of 7 hours, at reflux, at which time it is determined by GLC analysis to contain 1% of a mixture of 3- and 4-(4'-methyl-4'-hydroxyamyl)-Δ³-cyclohexene carboxyaldehyde. 100 ml of tetrahydrofuran is added and the reaction mass is stirred at room temperature for a period of 3 hours without any apparent change of concentration of a mixture of 3-and 4-(4'-methyl-4'-hydroxyamyl)-Δ³-cyclohexene carboxaldehyde in the reaction mass. The reaction mass is then brought to reflux for a period of 2 hours. 50 Grams of formic acid is added, and the reaction mass is maintained at room temperature for a period of 12 hours after which time it is determined to contain 1.5% of a mixture of 3- and 4-(4'-methyl-4'-hydroxyamyl)-Δ³-cyclohexene carboxaldehyde. Following 4 hours at reflux the reaction mass is determined to contain 1.9% of a mixture of 3- and 4-(4'-methyl-4'-hydroxyamyl)-Δ³-cyclohexene carboxaldehyde. At this point 100 grams of acetic acid is added to the reaction mass, and the reaction mass is then stirred for 2 1/2 hours at room temperature (no change in percentage of the mixture of 3- and 4-(4'-methyl-4'-hydroxyamyl)-Δ³-cyclohexene carboxaldehyde). The reaction mass is then refluxed for a period of 7 1/2 hours after which time it is determined that there is a concentration of 4% desired product in the reaction mass. At the end of this period of time the catalyst is filtered, and the reaction mass is washed neutral. It is then determined to contain:
  18.0% Solvent
  76% Myrac Aldehyde
  4% Mixture of 3- and 4-(4'-methyl-4'-hydroxyamyl)-Δ³-cyclohexene carboxaldehyde

EXAMPLE VI

Into a 500 ml reaction flask equipped with stirrer, thermometer and reflux condenser, the following materials are added:

| Ingredient | Quantity |
|---|---|
| myrac aldehyde | 100 grams |
| acetic acid | 100 grams |
| sulfuric acid (64%) | 50 grams |

Samples are taken at the following intervals indicating the following percentages desired product of 4-(4'-methyl-4'-hydroxyamyl)-Δ³-cyclohexene carboxaldehyde:

| Time of Reaction | Temperature | % of Desired Product (By area normalization) |
|---|---|---|
| 15 min. | 78° C | 33% |
| 75 min. | 40° C | 58% |
| 195 min. | 33° C | 69% |
| 300 min. | 33° C | 73.7% |

The actual reaction mass contains the following at the end of the reaction (internal standard):
83% Solvent
6.1% Myrac Aldehyde
10.2% Desired Product mixture of 3- and 4-(4'-methyl-4'-hydroxyamyl)- Δ³-cyclohexene carboxaldehyde

EXAMPLE VII

Into a 500 ml reaction flask equipped with stirrer, thermometer and reflux condenser the following materials are added:

| Ingredient | Quantity |
|---|---|
| myrac aldehyde | 100 grams |
| acetic acid | 100 grams |
| paratoluene sulfonic acid | 10 grams |

The reaction mass is stirred at room temperature and samples are taken at various intervals indicating various percentages of the desired product, a mixture of 3- and 4-(4'-methyl-4'-hydroxyamyl)-Δ³-cyclohexene carboxaldehyde:

| Time of Reaction | % Desired Product |
|---|---|
| 30 min. | 5.6% |
| 90 min. | 14.8% |
| 210 min. | 21% |
| 330 min. | 22.6% |

10 Grams of water is then added to the reaction mass and it is stirred for another 1/2 hour at which time 18.9% of a mixture of 3- and 4-(4'-methyl-4'-hydroxyamyl)-Δ³-cyclohexene carboxaldehyde is indicated to be formed. The reaction mass is stirred for another 4 hours at room temperature, at the end of which time 28% of a mixture of 3- and 4-(4'-methyl-4'-hydroxyamyl)-Δ³-cyclohexene carboxaldehyde is indicated to be present on a reaction mass (solventfree basis). GLC analysis indicates the following raw percentages:
91.6% Solvent
5.3% Myrac aldehyde
2.6% mixture of 3- and predominantly, 4-(4'-methyl-4'-hydroxyamyl)-Δ³-cyclohexene carboxaldehyde
The mixture of 3- and 4-(4'-methyl-4'-hydroxyamyl)-Δ³-cyclohexene carboxaldehyde is then distilled from the reaction mass and is used in the following Examples VIII-XV.

EXAMPLE VIII

A perfume composition of the "Fougére" type is produced

| Part by Weight | Ingredients |
|---|---|
| 50 | Cinnamic alcohol |
| 40 | Musk ambrette |
| 5 | Vanillin |
| 80 | Coumarin |
| 10 | Oakmoss resinoid |
| 125 | Linalool |
| 150 | Linalyl acetate |
| 50 | Benzyl acetate |
| 70 | Phenylethanol |
| 100 | Oil of bergamot |
| 150 | Oil of lavender |
| 50 | Geranium oil (Bourbon) |
| 50 | Sandalwood oil E.I. |
| 5 | Eugenol |
| 15 | Isoeugenol |
| 20 | Amyl salicylate |
| 20 | Benzyl salicylate |
| 20 | Product produced according to Ex. I containing major proportion of a mixture of 3- and 4-(4'-methyl-4'-hydroxyamyl)-Δ³-cyclohexene carboxaldehyde |
| 1010 | |

This product produced by Example I imparts a very sweet lilac lily aromatic odor to this "Fougére" formulation.

EXAMPLE IX

A perfume composition of the "Rose" type is produced by admixing the following ingredients:

| Parts by Weight | Ingredients |
|---|---|
| 20 | Phenylethyl phenyl acetate |
| 40 | Phenylethyl salicylate |
| 150 | Geraniol |
| 240 | Phenylethanol |
| 150 | Citronellol |
| 20 | Sandalwood oil E.I. |
| 75 | Nonanediol diacetate - 1,3 |
| 50 | Geranyl acetate |
| 20 | Geranyl phenylacetate |
| 20 | Citronellyl formate |
| 25 | Phenylethyl acetate |
| 60 | Phenylethyl propionate |
| 20 | Phenylacetaldehyde 50% in diethylphthalate |
| 20 | Phenylacetaldehyde 1,3-butyleneglycolacetal |
| 10 | Eugenol |
| 10 | Methylisoeugenol |
| 50 | Alpha-hexylcinnamic aldehyde |
| 40 | Product produced by the process of Ex. III containing a major proportion of a mixture of 3- and 4-(4'-methyl-4'-hydroxyamyl)-Δ³-cyclohexene crboxaldehyde |
| 1030 | |

This "Rose" perfume has a sweet floral aroma enhanced by addition thereto of the product produced according to Example III.

EXAMPLE X

A perfume composition of the "Bouquet" typs is produced by admixing the following ingredients:

| Parts by Weight | Ingredients |
|---|---|
| 20 | Musk ambrette |
| 40 | Heliotropine |
| 100 | Benzyl acetate |
| 80 | 4-tert.butyl cyclohexyl acetate |
| 130 | Alpha-hexylcinnamic aldehyde |

-continued

| Parts by Weight | Ingredients |
|---|---|
| 40 | Alpha-amylcinnamic aldehyde |
| 30 | Linalyl acetate |
| 80 | Terpineol |
| 80 | Geranyl acetate |
| 80 | Linalool |
| 100 | Alpha-methyl ionone |
| 25 | Methyl isoeugenol |
| 15 | Isoeugenol |
| 40 | Geraniol |
| 60 | Phenylethanol |
| 20 | Styrallyl acetate |
| 50 | Vetiveryl acetate |
| 5 | 10-undecene-1-al |
| 5 | Product produced according to Example IV containing a major proportion of a mixture of 3-4-(4'-methyl-4'-hydroxyamyl)-$\Delta^3$-cyclohexene carboxaldehyde |
| 1000 | |

Addition of the product produced according to Example IV imparts a sweet lilac-lily nuance to this Bouquet type perfume composition.

EXAMPLE XI

PREPARATION OF A COSMETIC POWDER COMPOSITION

A cosmetic powder is prepared by mixing in a ball mill, 100 g of talcum powder with 0.25 g of the mixture containing 3- and predominantly 4-(4'-methyl-4'-hydroxyamyl)-$\Delta^3$-cyclohexene carboxaldehyde prepared according to Example I. It has an excellent sweet, lilac-lily aroma.

EXAMPLE XII

PERFUMED LIQUID DETERGENT

Concentrated liquid detergents with a sweet, lilac-lily odor are prepared containing 0.10%, 0.15% and 0.20% of the mixture containing 3- and predominantly 4-(4'-methyl-4'-hydroxyamyl)-$\Delta^3$-cyclohexene carboxaldehyde prepared according to Example VI. They are prepared by adding and homogeneously mixing the appropriate quantity of the mixture containing 3- and predominantly 4-(4'-hydroxyamyl)-$\Delta^3$-cyclohexene carboxaldehyde in the liquid detergent. The detergents all possess a sweet, lilac-lily fragrance, the intensity increasing with greater concentrations of the mixture containing 3-and predominantly 4-(4'-hydroxyamyl)-$\Delta^3$-cyclohexene carboxaldehyde.

EXAMPLE XIII

PREPARATION OF A COLOGNE AND HANDKERCHIEF PERFUME

A mixture containing 3-and predominantly 4-(4'-methyl-4'-hydroxyamyl)-$\Delta^3$-cyclohexene carboxaldehyde prepared according to the process of Example II is incorporated in a cologne at a concentration of 2.5% in 85% aqueous ethanol and into a handkerchief perfume at a concentration of 20% (in 95% aqueous ethanol). A distinct and definite sweet, lilac-lily fragrance is imparted to the cologne and to the handkerchief perfume.

EXAMPLE XIV

PREPARATION OF A COLOGNE AND HANDKERCHIEF PERFUME

The composition of Example IX is incorporated in a cologne at a concentration of 2.5% in 85% aqueous ethanol; and into a handkerchief perfume at a concentration of 20% (in 95% aqueous ethanol). The use of the mixture containing 3- and 4-(4'-methyl-4'-hydroxyamyl)-$\Delta^3$-cyclohexene carboxaldehyde in the composition of Example IX affords a distinct and definite strong bouquet aroma with sweet, lilac-lily notes to the handkerchief cologne and perfume.

EXAMPLE XV

PREPARATION OF SOAP COMPOSITION

One hundred grams of soap chips are mixed with one gram of a mixture containing 3- and 4-(4'-methyl-4'-hydroxyamyl)-$\Delta^3$-cyclohexene carboxaldehyde produced according to Example III, until a substantially homogeneous composition is obtained. The perfumed soap composition manifests an excellent sweet, lilac-lily aroma.

EXAMPLE XVI

PREPARATION OF A DETERGENT COMPOSITION

A total of 100 g of a detergent powder is mixed with 0.15 g of the mixture containing 3- and 4-(4'-methyl-4'-hydroxyamyl)-$\Delta^3$-cyclohexene carboxaldehyde prepared according to Example IV until a substantially homogeneous composition is obtained. This composition has an excellent sweet, lilac-lily aroma.

EXAMPLE XVII

PART A

Into a 250 ml reaction flask equipped with stirrer and thermometer are added the following materials:

| Ingredient | Quantity |
|---|---|
| Dowex®50W-X4 cation exchange resin (sulfonated co-polymer of styrene and divinyl benzene containing 4% divinyl benzene monomeric units produced by the Dow Chemical Company of Midland, Michigan; moisture content 65.3%; 50–100 mesh) | 100 g |
| myrac aldehyde | 100 g |
| acetic acid | 100 g |

The reaction mass is stirred at room temperature for a period of 33 hours with samples taken and analyzed for the presence of a mixture of 3- and 4-(4'-hydroxyamyl)-$\Delta^3$ -cyclohexene carboxaldehyde at varying intervals:

| Time | % Lyral in Reaction Mass |
|---|---|
| 9 hours | 8% |
| 22 hours | 16% |
| 33 hours | 22.5% |

The reaction mass is filtered, neutralized and fractionally distilled, the lyral being distilled at 141°–153° C at 1.4–3.9 mm Hg pressure. The distillate thus collected is then fractionated using a 12 × 1 inch Goodloe packed column to yield product having a boiling point of 125°–126° C at 0.7 mm Hg pressure.

PART B

The procedure of Part A is repeated except the temperature at which the reaction is carried out is between 60°–62° C and the time of reaction is 3 ½ hours. The following table sets forth the time of reaction, the temperature and the percent lyral in the reaction mass:

| Time | Temperature | Percent |
| --- | --- | --- |
| 45 minutes | 61° C | 19.5% |
| 2½ hours | 60° C | 7.0% |
| 3½ hours | 61° C | 3.5% |

PART C

CONTINUOUS HYDRATION OF MYRAC ALDEHYDE USING DOWEX ® 50W-X4

A solution is formed from the following ingredients:

| Ingredient | Quantity |
| --- | --- |
| myrac aldehyde | 500 g |
| acetic acid | 1000 g |
| deionized water | 180 g |

50 g of Dowex 50W-X4 (preferably washed with 200 g 10% sulfuric acid and rinsed with deionized water) is rinsed into a water jacketed chromatography column (20 mm) using 80% acetic acid. The column is then rinsed with 500 g of 80% acetic acid. After that, the myrac aldehyde/acetic acid/water solution is allowed to flow through the chromatography column by gravity feed. The temperature of the column is varied between 26° and 50° C over a period of 6 hours. The following table sets forth the time of reaction, temperature of the column and percent lyral in the eluate as well as the total weight of eluate:

| Time | Temperature | Ratio Myrac Aldehyde:Lyral | Weight of Eluate |
| --- | --- | --- | --- |
| 30 minutes | 26° C | 0 | 68 g |
| 2 hours | 36° C | 0 | 72 g |
| 4 hours | 27° C | 0 | 80 g |
| 5 hours | 27–49° C | 11:1 | 83 g |
| 6 hours | 50° C | 12.65:1 | 90 g |

PART D

The procedure of Part C is repeated except that the chromatography column is operated between 50° and 60° C and the following results are achieved:

| Time | Temperature | Ratio Myrac Aldehyde:Lyral | Weight of Eluate |
| --- | --- | --- | --- |
| 1½ hours | 57–60° C | 20:1 | 171 g |
| 3 hours | 50° C | 25:1 | 125 g |
| 4 hours | 55° C | 20:1 | 98 g |

PART E

Into a 250 ml reaction flask equipped with stirrer and thermometer the following materials are added:

| Ingredient | Quantity |
| --- | --- |
| myrac aldehyde | 25 g |
| Dowex®50W-X4 | 50 g |
| glacial acetic acid | 50 g |

The reaction mass is stirred at room temperature for a period of 48 hours without production of any lyral. It is then heated up to 60° C and maintained at that temperature for 7 hours.

A 20 cc sample is removed and placed in a separatory funnel. To this sample is added 100 ml water and 50 cc benzene. The resulting mixture is shaken vigorously and the water phase is separated from the resin/oil layer. The oil layer is washed neutral with sodium bicarbonate solution and dried over anhydrous magnesium sulfate. The benzene is then evaporated and the oil layer is analyzed using a preparative GLC. The resulting ratio of lyral:myrac aldehyde is 43.5:54.6.

The GLC profile is set forth in FIG. 1.

PART F

Into a 2 liter reaction flask equipped with stirrer, thermometer and reflux condenser the following materials are placed:

| Ingredient | Quantity |
| --- | --- |
| myrac aldehyde | 196 g (1 mole) |
| Dowex®50W-X4 | 583 g |
| water | 217 ml |

Figure 2:
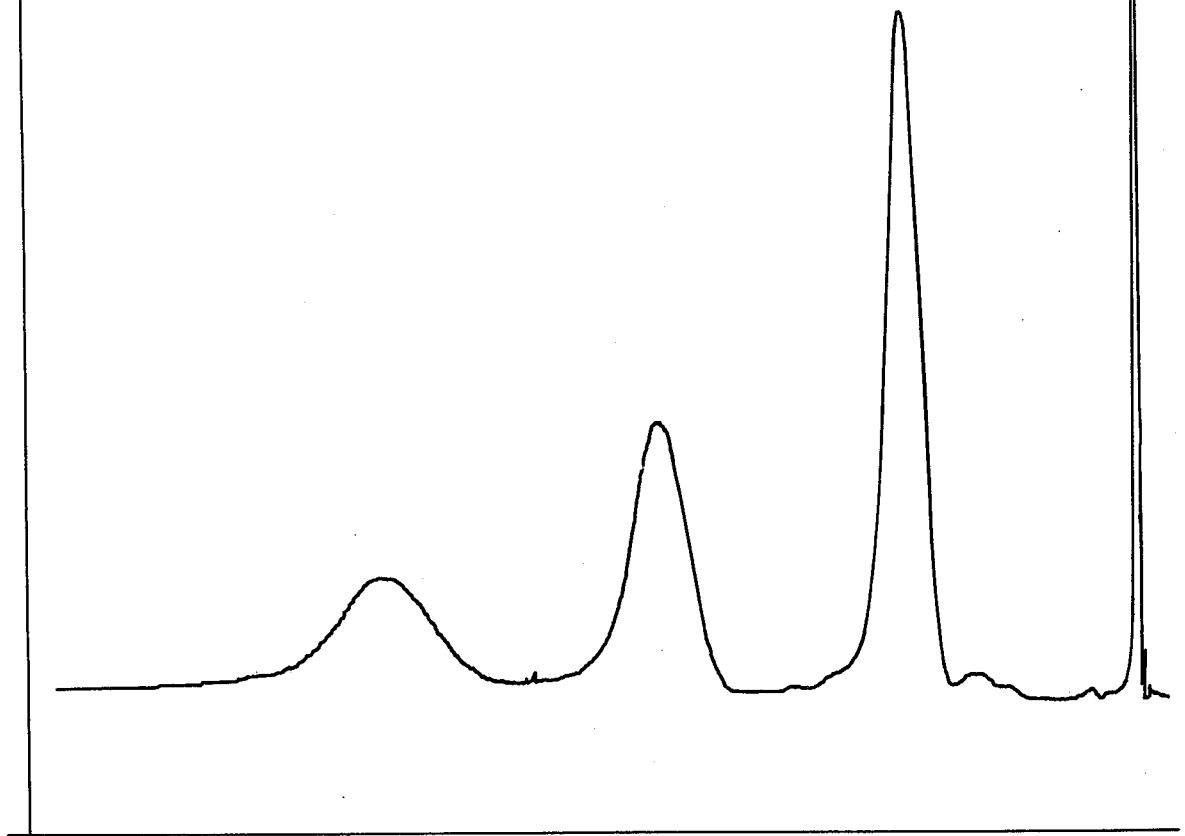
FIG. 2 is a GLC profile of the reaction product of Example XVI, Part F.

The reaction mass is heated to 60° C and maintained at that temperature with stirring for a period of 89 hours. At the end of the 89 hour period, a 20 cc sample is removed and placed in a separatory funnel. 100 ml of water is added to the solution with 50 cc benzene. The resulting mixture is shaken vigorously and the oil phase is separated and dried over anhydrous magnesium sulfate. The thus dried material is evaporated on a Rinco evaporator at 50° C GLC and Infrared analyses indicate that 29.4% lyral is formed. The ratio of lyral:myrac aldehyde is 32.5:64.2. FIG. 2 sets forth the GLC profile for the resulting product.

PART G

Into a 2 liter reaction flask equipped with stirrer, thermometer, reflux condenser and nitrogen blanket, the following materials are added:

| Ingredient | Quantity |
| --- | --- |
| myrac aldehyde | 196 g |
| Dowex®50W-X4 | 583 g |
| water | 67 ml |
| glacial acetic acid | 180 g (3 moles) |

Figure 3:
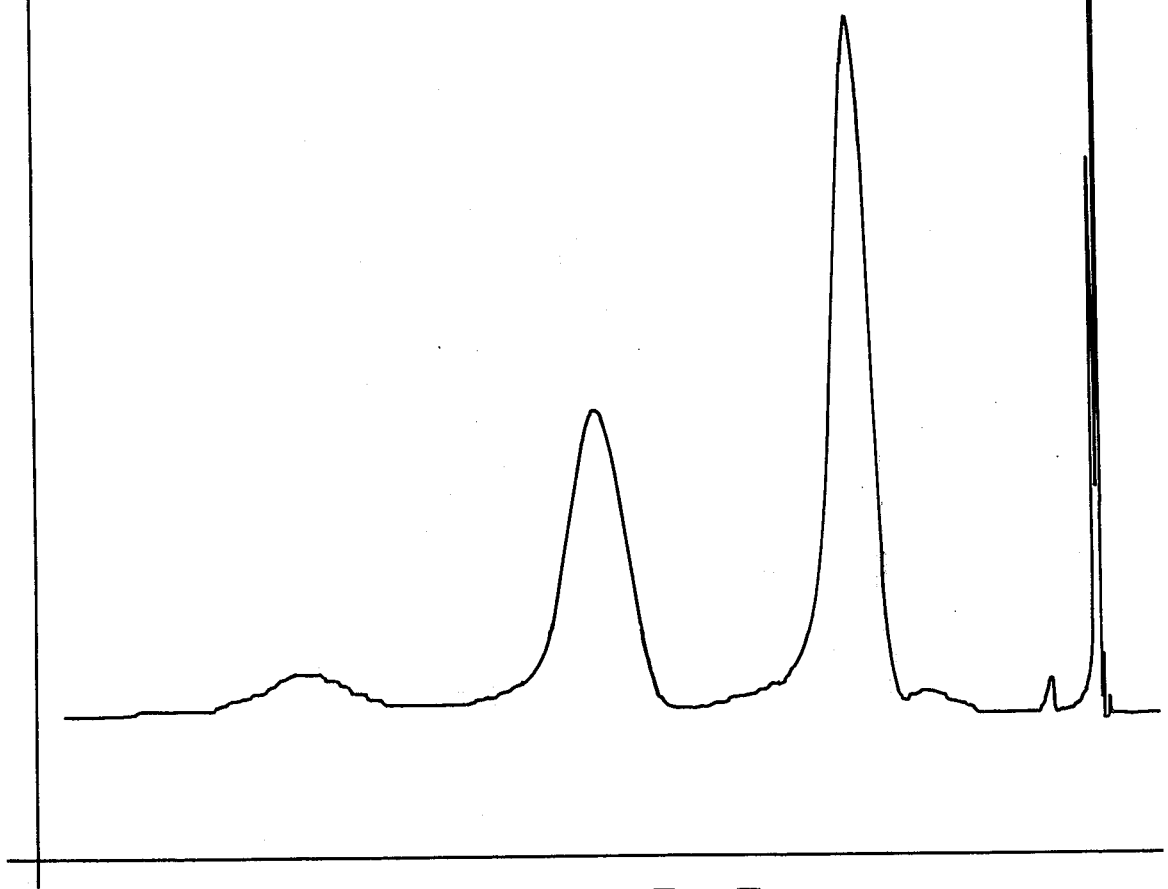
FIG. 3 is a GLC profile of the reaction product of Example XVI, Part G.

The reaction mass is heated with stirring to 60° C and maintained at that temperature for a period of 48 hours. At the end of the 48 hour period a 20 cc sample is removed therefrom and worked up in accordance with the procedure of Part F. GLC, Infrared and Mass Spectral analyses indicate the formation of 8.0% lyral. The ratio of myrac aldehyde:lyral is 87.7:8.0. FIG. 3 sets forth the GLC profile for the reaction product at the end of the 48 hour period.

PART H

Into a 2 liter reaction flask equipped with stirrer, thermometer, reflux condenser and nitrogen blanket, the following materials are added:

| Ingredient | Quantity |
|---|---|
| myrac aldehyde | 196 g |
| Dowex®50W-X4 | 620 g |
| acetic acid | 180 g (3 moles) |

Figure 4:
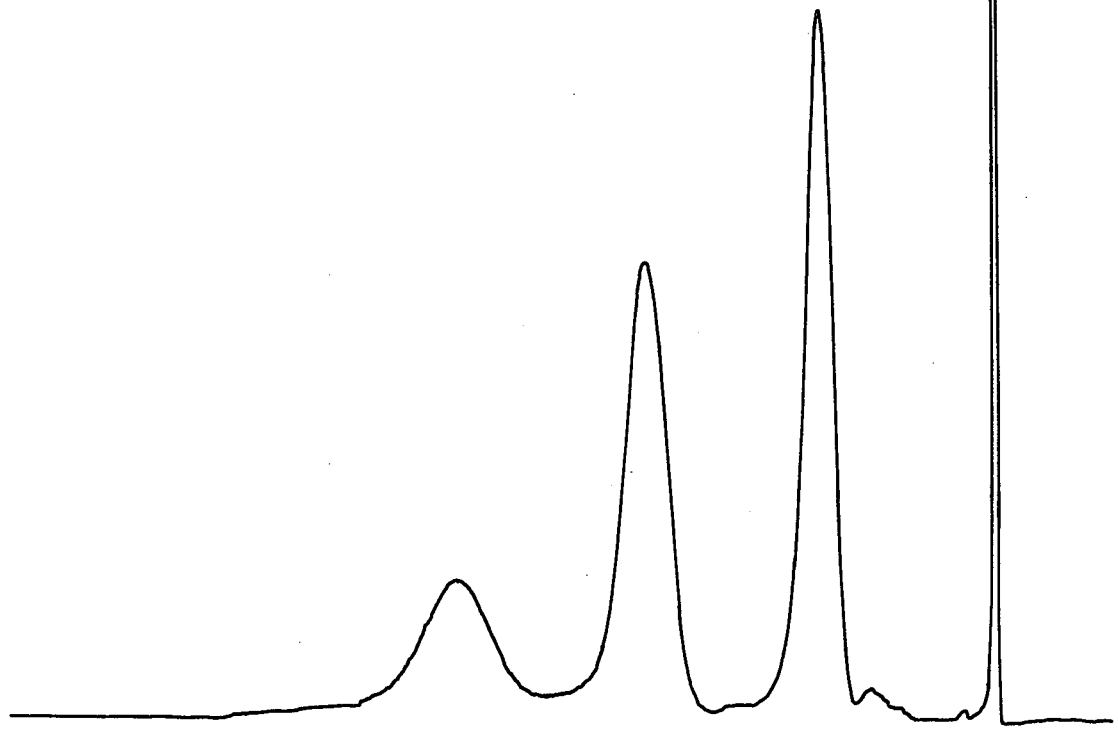
FIG. 4 is a GLC profile of the reaction product of Example XVI, Part H.

The reaction mass is heated up to 60° C with stirring and maintained at that temperature for 48 hours. The reaction mass is then worked up in accordance with the procedure of Part F. GLC, Infrared and Mass Spectral analyses yield the information that 25.3% lyral is produced. The ratio of lyral:myrac aldehyde is 24.8:74.9. FIG. 4 sets forth the GLC profile for the reaction product at the end of the 48 hour period.

PART I

Into a 2 liter raction flask equipped with stirrer, thermometer and reflux condenser the following materials are added:

| Ingredient | Quantity |
|---|---|
| myrac aldehyde | 98 g (0.5 moles) |
| Dowex®50W-X4 | 620 g |
| glacial acetic acid | 240 g (4 moles) |

The reaction mass is heated to 60° C and maintained at that temperature for a period of 24 hours, after which time it is worked up according to the procedure of Part F. GLC, Infrared and Mass Spectral analyses yield the information that 33.6% by-product is produced with a ratio of lyral:myrac aldehyde being 33.6:57.2.

Figure 5:
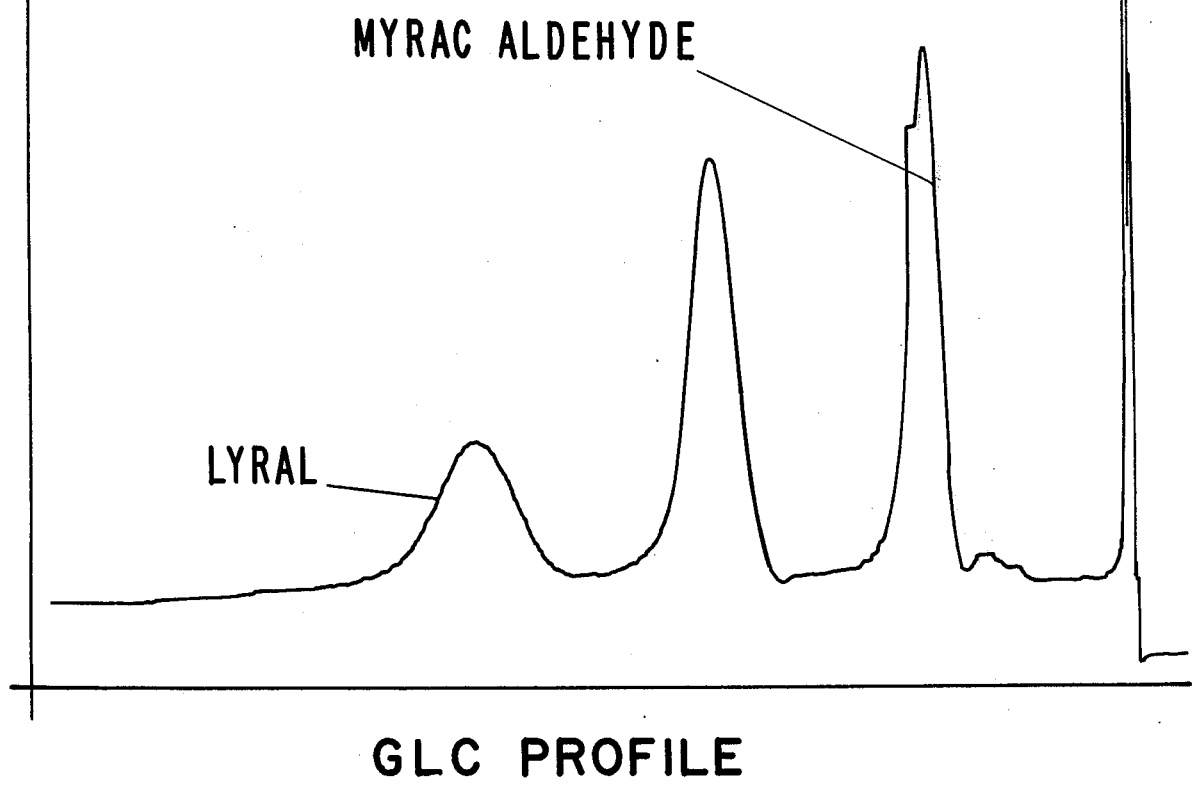
FIG. 5 is a GLC profile of the reaction product of Example XVI, Part I.

FIG. 5 sets forth the GLC profile for the reaction product at the end of the 24 hour period.

EXAMPLE XVIII

A clear, single phase solution is composed of 90 g myrac aldehyde, 100 g acetic acid and 18 g deionized water. This solution is admixed with 20 g of "amberlyst 15" cation exchange resin, produced by the Rohm and Haas Company of Philadelphia, Pennsylvania. Amberlyst 15 is a co-polymer of styrene and divinyl benzene, the monomeric units of divinyl benzene being equal to the monomeric units of styrene.

The reaction mass is stirred at temperatures of from 25°–80° C and samples are taken at different times and analyzed for percent lyral. The following table sets forth the time of reaction, temperature of reaction and percent lyral formed:

| Time | Temperature | Percent Lyral | |
|---|---|---|---|
| 2½ hours | 25–65° C | 3.2% | |
| 3½ hours | 65–64° C | 21% | |
| 4½ hours | 64–65° C | 29.3% | |
| 5 hours | 65–85° C | 11.9% | |
| 5¼ hours | 85–86° C | 14.3% | (by internal standards) |
| | | and | |
| | | 36.9% | (by area normalization) |

100 g of toluene is added and the reaction mass is washed with water and saturated sodium carbonate. The reaction mass is then evaporated and distilled yielding lyral which has a boiling point of 133°–135° C at 0.5–0.9 mm Hg pressure.

EXAMPLE XIX

Into a 500 ml reaction flask equipped with stirrer, thermometer and reflux condenser the following materials are added:

| Ingredient | Quantity |
|---|---|
| myrac aldehyde | 200 g |
| 30% aqueous sulfuric acid | 160 g |
| dimethyl formamide | 50 g |

The reaction mass is heated from 25° C up to reflux (117° C) and refluxing is continued for a period of 5 hours. At the end of the 4 hour period of refluxing, an additional 100 g of dimethyl formamide is added. Samples are taken at various times and analyzed using GLC analysis, yielding the following results:

| Time | Temperature | Percent Lyral Formed |
|---|---|---|
| 1½ hours | 117° C | 4.0% |
| 3¼ hours | 115° C | 4.6% |
| 5 hours | 114° C | 2.8% |

EXAMPLE XX

Reaction:

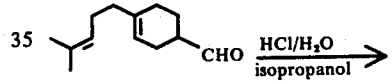

$$\text{HCl/H}_2\text{O} \xrightarrow{\text{isopropanol}}$$

Into a 250 ml reaction flask equipped with stirrer, thermometer and reflux condenser the following materials are added:

| Ingredient | Quantity |
|---|---|
| myrac aldehyde | 19.2 g (0.1 mole) |
| 1 molar hydrochloric acid | 100 ml (0.1 mole) |
| isopropyl alcohol | 100 ml |

The reaction mass is refluxed with stirring for a period of 4 hours.

100 ml water is then adder and the resulting aqueous layer is extracted with three 50 ml portions of diethyl ether. The ether extracts are combined and washed with three 50 ml portions of saturated sodium bicarbonate solutions followed by three 50 ml portions of water. The ether extract is then dried with anhydrous magnesium sulfate, filtered and concentrated. GLC analysis indicates the ratio of 49% myrac aldehyde to 47% lyral. The quantity of lyral formed is confirmed by NMR and Mass Spectral analyses.

Figure 6:
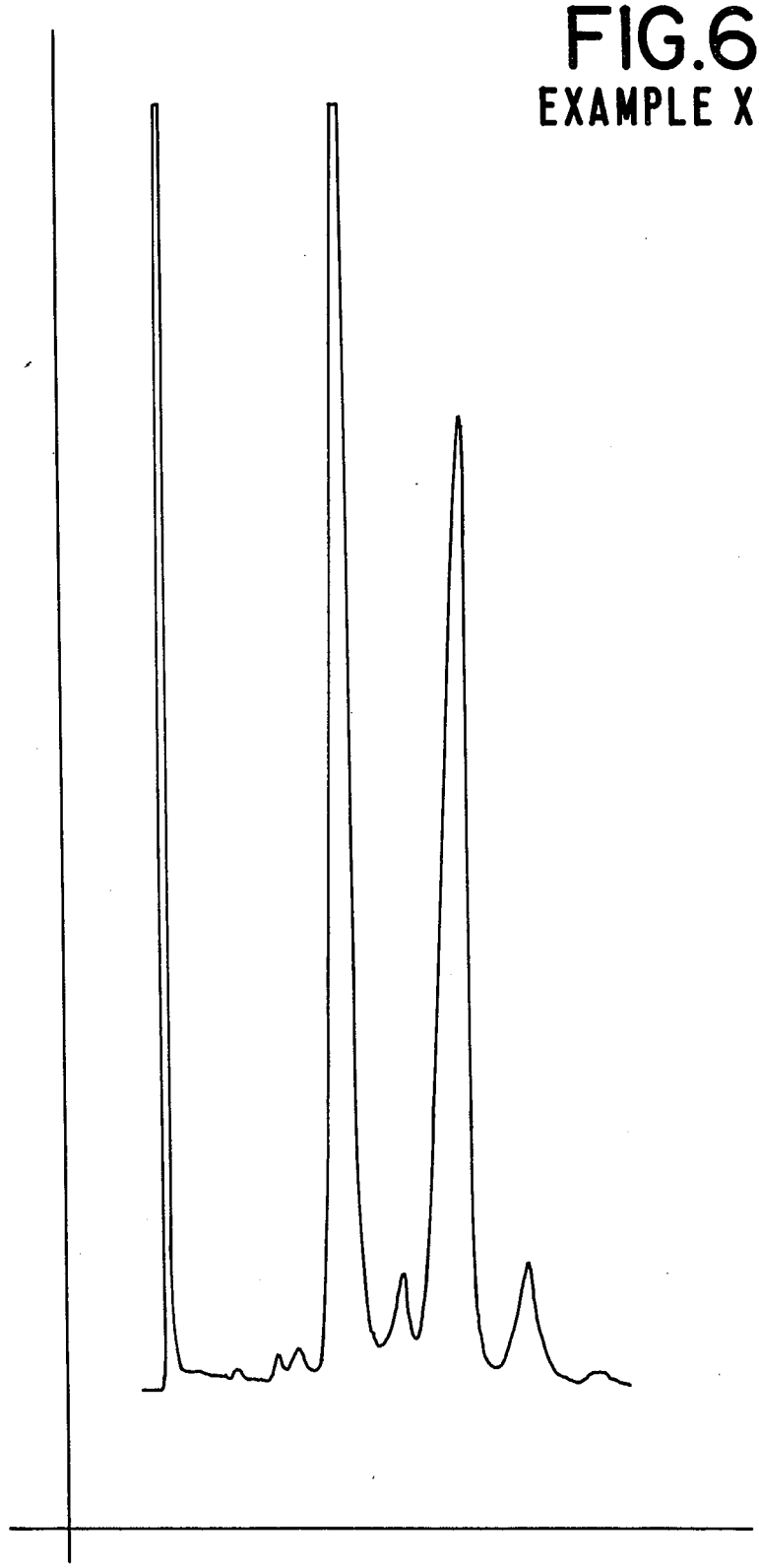
FIG. 6 is a GLC profile of the reaction product of Example XIX.
Figure 7:
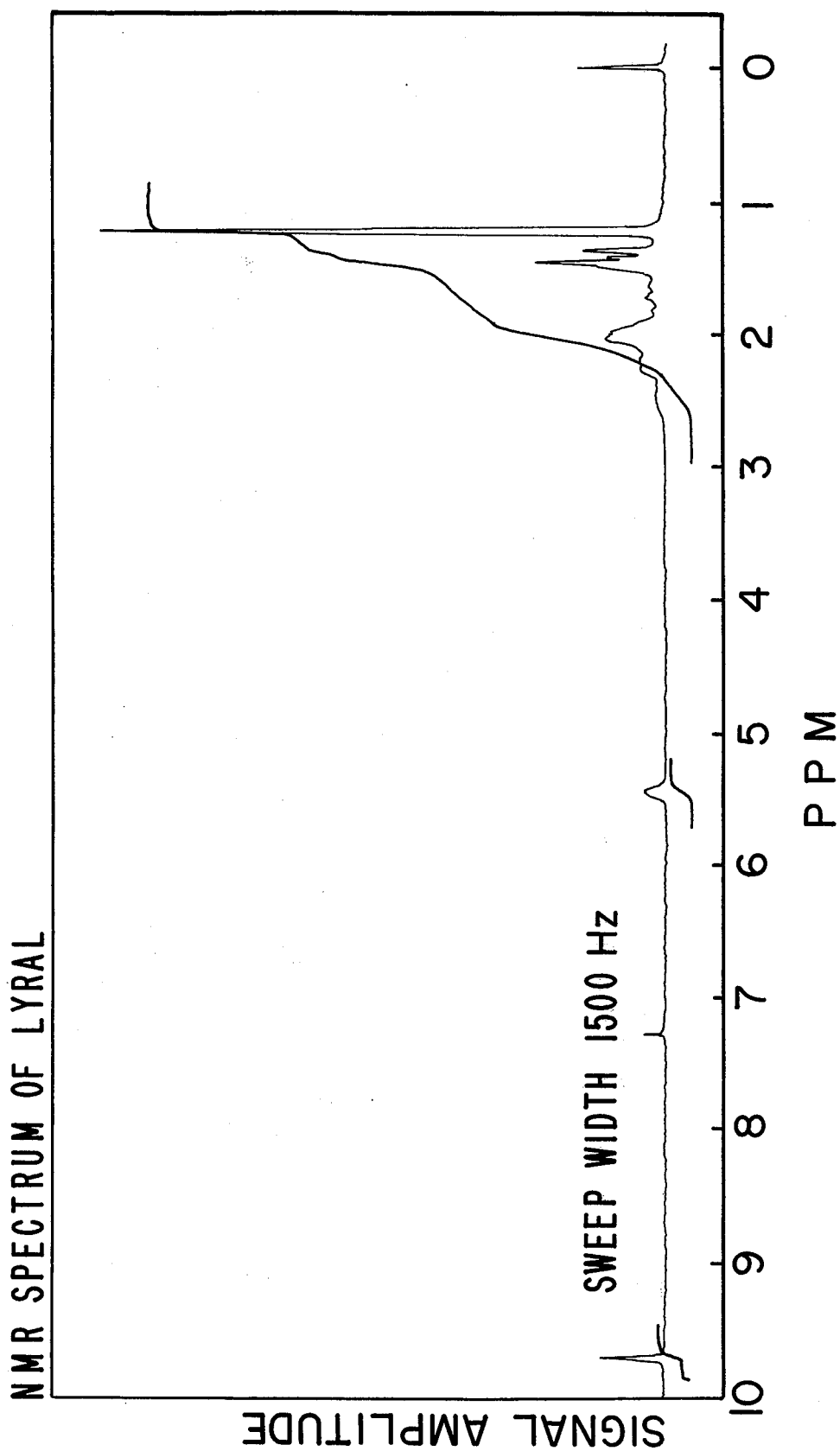
FIG. 7 is the NMR spectrum for the lyral produced according to the process of Example XIX.
Figure 8:
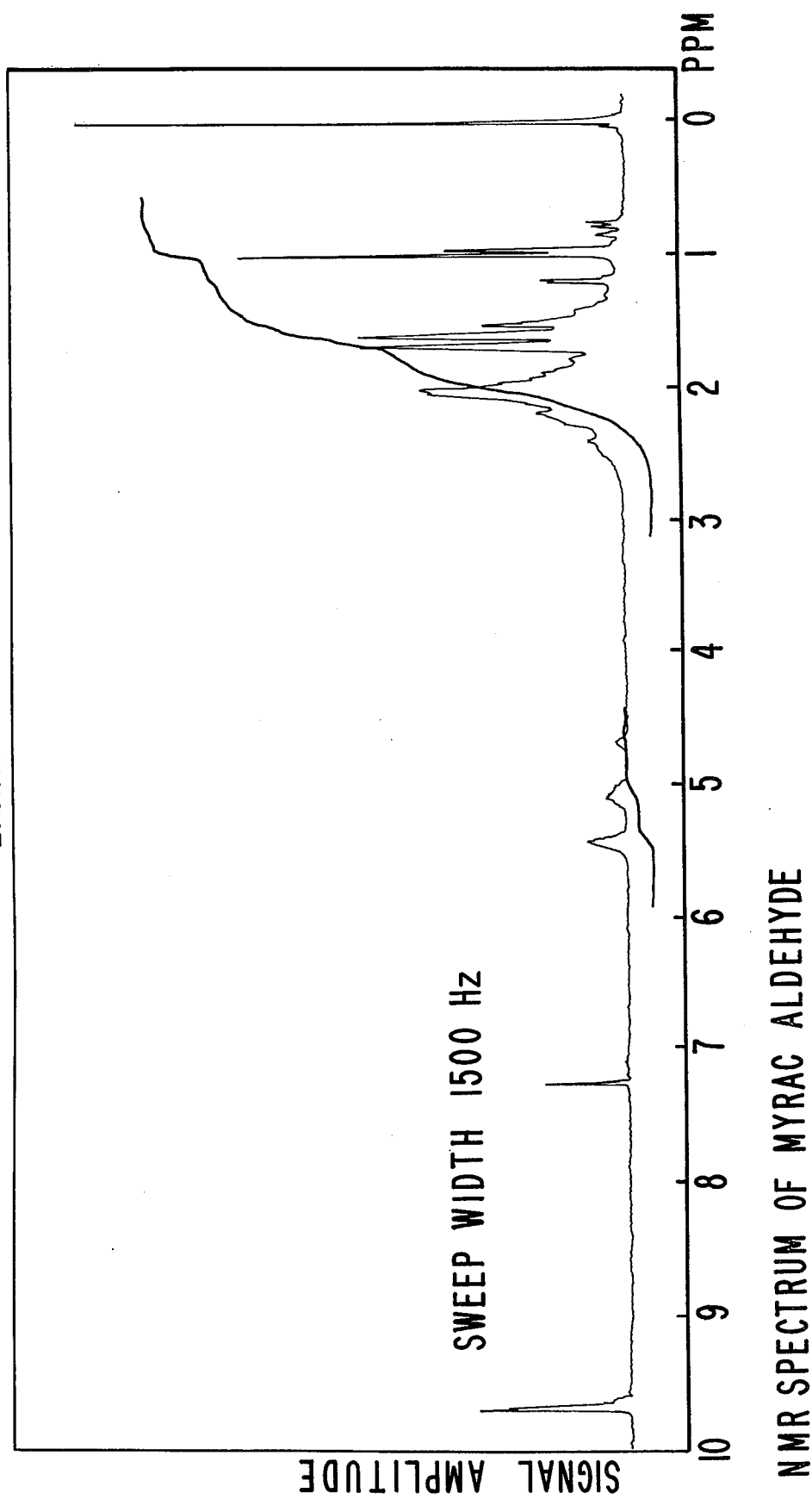
FIG. 8 is the NMR spectrum for the myrac aldehyde produced according to the process of Example XIX.
Figure 9:
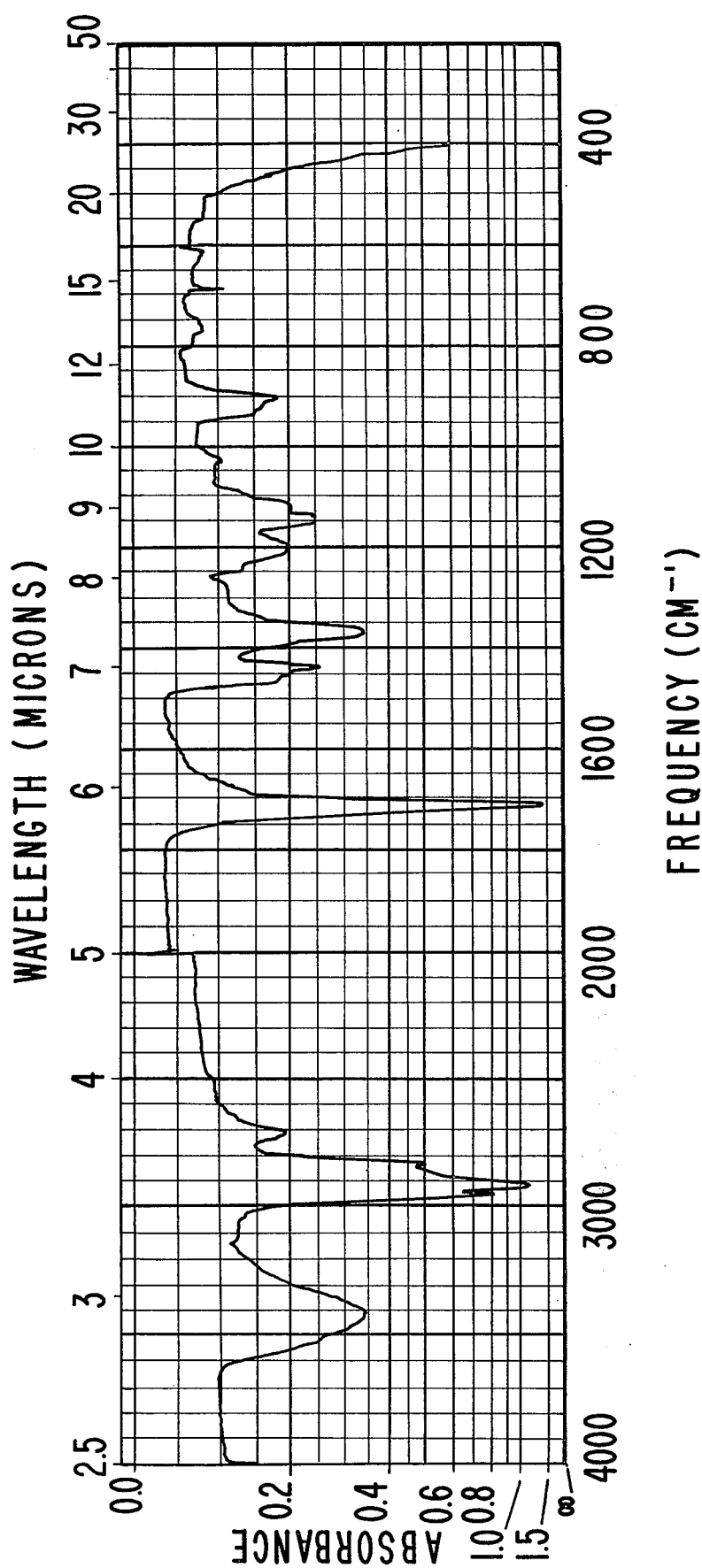
FIG. 9 is the Infrared spectrum for the lyral produced according to the process of Example XIX.

The GLC profile is set forth in FIG. 6. The lyral (mixture of 3- and 4-(4'-methyl-4'-hydroxyamyl)-$\Delta^3$-cyclohexene carboxaldehyde) is then distilled from the reaction mass and is used in the following Examples XXI-XXIX. The NMR spectrum for the lyral thus produced is set forth in FIG. 7. The NMR spectrum for myrac aldehyde is set forth in FIG. 8. The Infrared spectrum for the lyral is set forth in FIG. 9. The Infrared spectrum for myrac aldehyde is set forth in FIG. 10.

EXAMPLE XXI

A perfume composition of the Fougere type is produced:

| Parts by Weight | Ingredients |
|---|---|
| 50 | Cinnamic Alcohol |
| 40 | Musk Ambrette |
| 5 | Vanillin |
| 80 | Coumarin |
| 10 | Oakmoss Resinoid |
| 125 | Linalool |
| 150 | Linalyl Acetate |
| 50 | Benzyl Acetate |
| 70 | Phenylethanol |
| 100 | Oil of Bergamot |
| 150 | Oil of Lavender 45/47 |
| 50 | Geranium Oil (Bourbon) |
| 50 | Sandalwood Oil E.I. |
| 5 | Eugenol |
| 15 | Isoeugenol |
| 20 | Amyl Salicylate |
| 20 | Benzyl Salicylate |
| 20 | Product produced according to Ex. XX containing a major proportion of 4-(4'-methyl-4'-hydroxyamyl)-$\Delta^3$-cyclohexene carboxaldehyde |
| 1010 | |

This product produced by Example XX imparts a very sweet lilac-lily aromatic odor to this Fougere formulation.

EXAMPLE XXII

A perfume composition of the "Rose" type is produced by admixing the following ingredients:

| Parts by Weight | Ingredients |
|---|---|
| 20 | Phenylethyl phenyl acetate |
| 40 | Phenylethyl salicylate |
| 150 | Geraniol |
| 240 | Phenylethanol |
| 150 | Citronellol |
| 20 | Sandalwood oil E.I. |
| 75 | Nonanediol diacetate - 1,3 |
| 50 | Geranyl acetate |
| 20 | Geranyl phenylacetate |
| 20 | Citronellyl formate |
| 25 | Phenylethyl acetate |
| 60 | Phenylethyl propionate |
| 20 | Phenylacetaldehyde 50% in diethylphthalate |
| 20 | Phenylacetaldehyde 1,3-butyleneglycolacetal |
| 10 | Eugenol |
| 10 | Methylisoeugenol |
| 50 | Alpha-hexylcinnamic aldehyde |
| 40 | Product produced by the process of Ex. XX containing a major proportion of 4-(4'-methyl-4'-hydroxyamyl)-$\Delta^3$-cyclohexene carboxaldehyde and a minor proportion of 3-(4'-methyl-4'-hydroxyamyl-$\Delta^3$-cyclohexene carboxaldehyde |
| 1030 | |

This Rose perfume has a sweet floral aroma enhanced by addition thereto of the product produced according to Example XX.

EXAMPLE XXIII

A perfume composition of the "Bouquet" type is produced by admixing the following ingredients:

| Parts by Weight | Ingredients |
|---|---|
| 20 | Musk ambrette |
| 40 | Heliotropine |
| 100 | Benzyl acetate |
| 80 | 4-tert.butyl cyclohexyl acetate |
| 130 | Alpha-hexylcinnamic aldehyde |
| 40 | Alpha-amylcinnamic aldehyde |
| 30 | Linalyl acetate |
| 80 | Terpineol |
| 80 | Geranyl acetate |
| 80 | Linalool |
| 100 | Alpha-methyl ionone |
| 25 | Methyl isoeugenol |
| 15 | Isoeugenol |
| 40 | Geraniol |
| 60 | Phenylethanol |
| 20 | Styrallyl acetate |
| 50 | Vetiveryl acetate |
| 5 | 10-undecene-1-al |
| 5 | Product produced according to Example XX containing a major proportion of 4-(4'-methyl-4'-hydroxyamyl)-$\Delta^3$-cyclohexene carboxaldehyde and a minor proportion of 3-(4'-methyl-4'-hydroxyamyl)-$\Delta^3$-cyclohexene carboxaldehyde |
| 1000 | |

Addition of the product produced according to Example XX imparts a sweet lilac-lily nuance to this Bouquet type perfume composition.

EXAMPLE XXIV

PREPARATION OF A COSMETIC POWDER COMPOSITION

A cosmetic powder is prepared by mixing in a ball mill, 100 g of talcum powder with 0.25 g of the mixture containing 3- and predominantly 4-(4'-methyl-4'-hydroxyamyl)-$\Delta^3$-cyclohexene carboxaldehyde prepared according to Example XX. It has an excellent sweet, lilac-lily aroma.

EXAMPLE XXV

PERFUMED LIQUID DETERGENT

Concentrated liquid detergents with a sweet, lilac-lily odor are prepared containing 0.10%, 0.15% and 0.20% of the mixture containing 3- and predominantly 4-(4'-methyl-4'-hydroxyamyl)-$\Delta^3$-cyclohexene carboxaldehyde prepared according to the process of Example XX. They are prepared by adding and homogeneously mixing the appropriate quantity of the mixture containing 3- and 4-(4'-methyl-4'-hydroxyamyl)-$\Delta^3$-cyclohexene carboxaldehyde in the liquid detergent. The detergents all possess a sweet, lilac-lily fragrance, the intensity increasing with greater concentrations of mixture containing 3- and 4-(4'-methyl-4'-hydroxyamyl)-$\Delta^3$-cyclohexene carboxaldehyde.

EXAMPLE XXVI

PREPARATION OF A COLOGNE AND HANDKERCHIEF PERFUME

A mixture containing 4-(4'-methyl-4'-hydroxyamyl)-$\Delta^3$-cyclohexene carboxaldehyde prepared according to the process of Example XX is incorporated in a cologne at a concentration of 2.5% in 85% aqueous ethanol and into a handkerchief perfume at a concentration of 20% (in 95% aqueous ethanol). A distinct and definite sweet, lilac-lily fragrance is imparted to the cologne and to the handkerchief perfume.

EXAMPLE XXVII

PREPARATION OF A COLOGNE AND HANDKERCHIEF PERFUME

The composition of Example XXIII is incorporated in a cologne at a concentration of 2.5% in 85% aqueous ethanol; and into a handkerchief perfume at a concentration of 20% (in 95% aqueous ethanol). The use of the mixture containing 4-(4'-methyl-4'-hydroxyamyl)-$\Delta^3$-cyclohexene carboxaldehyde in the composition of Example XXIII affords a distinct and definite strong bouquet aroma with sweet, lilac-lily notes to the handkerchief perfume and cologne.

EXAMPLE XXVIII

PREPARATION OF SOAP COMPOSITION

One hundred grams of soap chips are mixed with one gram of a mixture containing 4-(4'-methyl-4'-hydroxyamyl)-$\Delta^3$-cyclohexene carboxaldehyde produced according to Example XX, until a substantially homogeneous composition is obtained. The perfumed soap composition manifests an excellent sweet, lilac-lily aroma.

EXAMPLE XXIX

PREPARATION OF A DETERGENT COMPOSITION

A total of 100 g of a detergent powder containing sodium benzene sulfonate is mixed with 0.15 g of the mixture containing 4-(4'-methyl-4'-hydroxyamyl)-$\Delta^3$-cyclohexene carboxaldehyde prepared according to Example XX, until a substantially homogeneous composition is obtained. This composition has an excellent sweet, lilac-lily aroma.

What is claimed is:

1. A process for producing a mixture containing a major proportion of 4-(4'-methyl-4'-hydroxyamyl)-$\Delta^3$-cyclohexene carboxaldehyde having the structure:

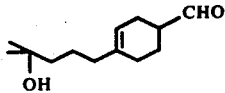

comprising the step of intimately admixing myrac aldehyde having the structure:

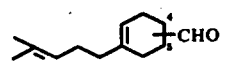

with a hydrating reagent selected from the group consisting of:
  i. mixture of lower alkanoic acid and p-toluenesulfonic acid;
  ii. mixture of 30% aqueous sulfuric acid and tetrahydrofuran;
  iii. mixture of 30% sulfuric acid and dimethyl formamide;
  iv. mixture of 50% sulfuric acid and tetrahydrofuran;
  v. mixture of 65% sulfuric acid and acetic acid;
  vi. mixture of methane sulfonic acid and tetrahydrofuran;
  vii. sulfonated co-polymer of styrene and divinyl benzene cation exchange resin;
  viii. mixture of (a) sulfonated co-polymer of styrene and divinyl benzene cation exchange resin and (b) lower alkanoic acid; or
  ix. mixture of aqueous hydrochloric acid and a lower alkanol at a temperature in the range of from 0° C up to 120° C, the reaction being carried out over a period of time varying from 1 hour up to 48 hours and the concentration of hydrating reagent in the reaction mass varying from about 3 up to about 50%, the reaction being carried out in the presence of water.

2. The process of claim 1 wherein the hydrating reagent is a mixture of lower alkanoic acid and p-toluenesulfonic acid.

3. The process of claim 1 wherein the hydrating reagent is a mixture of 30% aqueous sulfuric acid and tetrahydrofuran.

4. The process of claim 1 wherein the hydrating reagent is a mixture of 30% sulfuric acid and dimethyl formamide.

5. The process of claim 1 wherein the hydrating reagent is a mixture of 50% sulfuric acid and tetrahydrofuran.

6. The process of claim 1 wherein the hydrating reagent is a mixture of 65% sulfuric acid and acetic acid.

7. The process of claim 1 wherein the hydrating reagent is a mixture of methane sulfonic acid and tetrahydrofuran.

8. The process of claim 1 wherein the hydrating reagent is sulfonated co-polymer of styrene and divinyl benzene cation exchange resin.

9. The process of claim 1 wherein the hydrating reagent is a mixture of (a) sulfonated co-polymer of styrene and divinyl benzene cation exchange resin and (b) lower alkanoic acid.

10. The process of claim 1 wherein the hydrating reagent is a mixture of aqueous hydrochloric acid and isopropanol.

* * * * *